(12) United States Patent
Chen et al.

(10) Patent No.: US 10,918,479 B2
(45) Date of Patent: Feb. 16, 2021

(54) HEART VALVE PROSTHESIS

(71) Applicant: SHANGHAI MICROPORT CARDIOFLOW MEDTECH CO., LTD., Shanghai (CN)

(72) Inventors: Guoming Chen, Shanghai (CN); Yu Li, Shanghai (CN); Feng Huang, Shanghai (CN); Lei Huang, Shanghai (CN); Jianchao Han, Shanghai (CN); Yihao Duan, Shanghai (CN); Shaohui Chen, Shanghai (CN); Qiyi Luo, Shanghai (CN)

(73) Assignee: SHANGHAI MICROPORT CARDIOFLOW MEDTECH CO., LTD., Shanghai (CN)

( * ) Notice: Subject to any disclaimer, the term of this patent is extended or adjusted under 35 U.S.C. 154(b) by 186 days.

(21) Appl. No.: 16/160,857

(22) Filed: Oct. 15, 2018

(65) Prior Publication Data
US 2019/0046316 A1    Feb. 14, 2019

Related U.S. Application Data

(63) Continuation-in-part of application No. 14/769,991, filed as application No. PCT/CN2014/072489 on Feb. 25, 2014, now abandoned.

(30) Foreign Application Priority Data

Feb. 25, 2013    (CN) .......................... 2013 1 0064011

(51) Int. Cl.
*A61F 2/24*    (2006.01)

(52) U.S. Cl.
CPC .... *A61F 2/2418* (2013.01); *A61F 2210/0014* (2013.01); *A61F 2220/0075* (2013.01);
(Continued)

(58) Field of Classification Search
CPC .. A61F 2/24; A61F 2/2418; A61F 2/86; A61F 2/90; A61F 2250/0036; A61F 2230/001
See application file for complete search history.

(56) References Cited

U.S. PATENT DOCUMENTS

| 2,909,177 A | 10/1959 | Dowd et al. |
| 6,468,302 B2 | 10/2002 | Cox et al. |

(Continued)

FOREIGN PATENT DOCUMENTS

| CN | 2902226 Y | 5/2007 |
| CN | 101374477 A | 2/2009 |

(Continued)

*Primary Examiner* — Dinah Baria
(74) *Attorney, Agent, or Firm* — Muncy, Geissler, Olds & Lowe, P.C.

(57) ABSTRACT

A stent (1) used for a heart valve prosthesis and the heart valve prosthesis that includes the stent (1) and is used for heart valve replacement. The stent is configured to support a heart valve (3) and includes, along a longitudinal axis, an inflow section (8), an outflow section (6) and a transition section (7) between the inflow section (8) and the outflow section (6). The stent (1) has a contracted delivery configuration and an expanded deployed configuration. In the expanded deployed configuration, the inflow section (8) defines a concave contour that is complementary to a structure of a native valve annulus. The concave contour enables self-deployment and close adherence of the stent (1), thereby preventing its displacement and perivalvular leakage after implantation.

20 Claims, 3 Drawing Sheets

(52) U.S. Cl.
CPC . *A61F 2230/005* (2013.01); *A61F 2230/0054* (2013.01); *A61F 2230/0067* (2013.01); *A61F 2250/0039* (2013.01)

(56) References Cited

U.S. PATENT DOCUMENTS

| | | |
|---|---|---|
| 2006/0259136 A1 | 11/2006 | Nguyen et al. |
| 2006/0265056 A1 | 11/2006 | Nguyen et al. |
| 2009/0287299 A1 | 11/2009 | Tabor et al. |
| 2010/0049313 A1 | 2/2010 | Alon et al. |
| 2010/0094411 A1* | 4/2010 | Tuval ............... A61F 2/2427 623/2.1 |
| 2011/0172765 A1 | 7/2011 | Nguyen et al. |
| 2011/0238168 A1 | 9/2011 | Pellegrini et al. |
| 2011/0264196 A1 | 10/2011 | Savage et al. |
| 2012/0053685 A1* | 3/2012 | Cerf ............... A61F 2/2418 623/2.17 |
| 2012/0271398 A1 | 10/2012 | Essinger et al. |
| 2014/0200660 A1 | 7/2014 | Savage et al. |

FOREIGN PATENT DOCUMENTS

| | | |
|---|---|---|
| CN | 101953729 A | 1/2011 |
| CN | 102113921 A | 7/2011 |
| CN | 102481189 A | 5/2012 |
| CN | 102764169 A | 11/2012 |
| CN | 203280540 U | 11/2013 |

* cited by examiner

HEART VALVE PROSTHESIS

CROSS REFERENCE TO RELATED APPLICATIONS

This application is a Continuation-in-Part of co-pending application Ser. No. 14/769,991 filed on Aug. 24, 2015 for which priority is claimed under 35 U.S.C. § 120; and this application claims priority of PCT Application No. PCT/CN2014/072489 filed on Feb. 25, 2014; and claims priority of Application No. 201310064011.1 filed in CHINA on Feb. 25, 2013 under 35 U.S.C. § 119, the entire contents of all of which are hereby incorporated by reference.

TECHNICAL FIELD

This invention relates generally to heart valve prosthesis for use in minimally invasive heart valve replacement. In particular, the invention relates to a stent for use with a heart valve prosthesis, which can be deployed with close adherence to the anatomical structure of the heart and with minimal possibility of displacement and perivalvular leakage.

BACKGROUND

With the aging of the global population, aortic valve disease has become one of the most common cardiovascular diseases, with an incidence of 2%-5% in China and ranking as the third most frequent disease after coronary heart disease and hypertension in the West. Every year, tens of thousands of patients benefit from the surgical aortic valve replacement (SAVR). However, even in developed countries, there are still many patients with severe aortic valve disease who are inoperable due to a number of reasons such as late stages of the disease, advanced ages or multiple comorbidities. The debut of percutaneous artificial aortic valves, as well as the continuous performance improvement of such products, is undoubtedly a blessing for these patients because they provide an effective alternative for treating this disease.

Possible causes of aortic valve disease include birth defects, natural aging, infection, scarring, etc. Calcium may deposit around the aortic valve over time, which can narrow the aortic valve and/or make it close insufficiently, thus causing "aortic regurgitation". Most of patients with aortic valve disease suffer from angina, syncope and heart failure. Because these symptoms can lead to a serious decline in the quality of life and a significantly shortened survival time, effective treatment is necessary.

Since Cribier and colleagues first reported performing transcatheter aortic valve replacement (TAVR) in 2002, considerable effort has been devoted by researchers and physicians all over the world in basic and clinical studies in this art. These studies have achieved good clinical results and showed that this novel technology is safe and effective for patients who are inoperable or whose reception of surgical valve replacement is associated with a high risk. Compared with the surgical approach, percutaneous aortic valve replacement eliminates the need for open-heart procedures or for the support of an extracorporeal circulation machine and provides the advantages such as minimal invasiveness, fewer complications, quick retrieve, less patient suffering and high acceptance. Despite the fact that most TAVR-treated patients are high-risk ones, the TAVR method can still achieve a 30-day survival rate of higher than 90% and significantly improved postoperative hemodynamic parameters.

After numerous modifications and improvements, representative heart valve prosthesis currently used in clinical practice are Edwards valve stent systems and CoreValve stent systems. An Edwards-Sapien prosthetic valve is formed of bovine pericardial tissue and is assembled by sutures onto a stent fabricated from stainless steel (or a cobalt-chromium alloy). The valve can be deployed at the native valve annulus by a balloon-expandable stent in an anterograde, retrograde, or transapical manner without the need for use of any delivery sheath. The prosthetic valves for clinical use are available in two sizes of 23 mm and 26 mm. The application Pub. No. WO2009/149462A2 described several examples of such aortic valves. A large number of clinical trials have been conducted with Edwards-Sapien aortic valves and are very fruitful. CoreValve systems are another kind of valve stents that have been successfully applied in clinical use, and were successfully applied in human for the first time in 2005. CoreValve prosthetic valves are tri-leaflet porcine pericardial valves sewn onto self-expanding nitinol stents that are currently available in three sizes of 26 mm, 29 mm and 31 mm. U.S. application Pub. No. US2011/0172765A1 provides examples of valves of this type. The CoreValve stent is made of nickel-titanium memory alloy and typically has: a leading section with a relatively low radial strength, configured for anchoring to the ascending aorta above the sinus of Valsalva; a convex-concave intermediate section affixed with leaflets, for avoiding obstruction of blood flow to the coronary arteries; and a trailing section with a relatively high radial strength, configured to be securely disposed in the aortic annulus. The latest clinical studies have proven good hemodynamic effects and a low 30-day mortality of 8%, which suggests their satisfactory safety profile.

However, those prosthetic aortic valves commercially available still have some insufficient or unreasonable features. For TAVR, whether the valve stent has been accurately positioned is directly related to the success of the operation. The surrounding tissue of native human aortic valve is complicated in structure, including the ostia of the left and right coronary arteries located above the aortic valve, the underlying left ventricle, interventricular septum and bundle branches, and the bicuspid valve on the right. Inaccurate deployment of the prosthesis is very likely to cause a fatal complication such as coronary artery ostium obstruction or bundle branch block. With regard to the above two representative valve systems (Edwards and CoreValve), their weakness lies in not allowing retrieve or relocation. Once an Edwards valve stent has been rapidly expanded by balloon inflation and deployed to the desired position, further adjustments of the Edwards valve stent are impossible. During the course of the deployment of a CoreValve valve stent, some degree of adjustment is allowed, however further adjustments of the CoreValve valve stent are impossible after completion of the deployment. As a result, if deployment location deviates from target or implantation of improper size stent happens, the possible occurrence of stent displacement will cause serious complication, which might threaten the patient's life. Further, in the clinical use, CoreValve valve stents are frequently reported to cause bundle branch damage due to excessive extension in the ventricle or displace from the deployment position after implantation.

The present invention aims to address one or more of the aforesaid and other problems of the prior art.

SUMMARY OF THE INVENTION

It is an objective of the present invention to provide a heart valve prosthesis having a valve stent that is capable of closely adhering to a native valve annulus and hence preventing perivalvular leakage.

It is another objective of the invention to provide a heart valve prosthesis that can be securely deployed with minimal possibility of displacement.

It is still another objective of the invention to provide a heart valve prosthesis, which can solve the problem of left bundle branch block caused by excessive extension of valve stent in the left ventricle.

It is still another objective of the invention to provide a heart valve prosthesis, which can solve the problem of obstruction of blood flow to the coronary artery ostia caused by valve design deficiencies or inaccurate deployment.

It is still another objective of the invention to provide a heart valve prosthesis, which can solve the problem of inaccurate deployment and many other problems arising from imaging errors occurring in the implantation process.

In accordance with the above objectives, the present invention provides a stent for use in a heart valve prosthesis, configured to support a heart valve and including, along a longitudinal axis, an inflow section, an outflow section and a transition section between the inflow and outflow sections. The stent has a contracted delivery configuration and an expanded deployed configuration. In the expanded deployed configuration, the inflow section has a concave contour that is complementary to a structure of a native valve annulus.

According to one embodiment, the stent is a self-expanding stent including a mesh having a plurality of mesh cells.

According to one embodiment, ones of the mesh cells in a portion of the inflow section corresponding to the concave contour are larger than remaining ones of the mesh cells in the inflow section.

According to one embodiment, in the expanded deployed configuration, the stent conically tapers from the inflow section toward the transition section and flares from the transition section toward the outflow section.

According to one embodiment, the inflow and outflow sections have ends slightly contracted so as to be tapered.

According to one embodiment, the inflow section is circumferentially composed of twelve mesh cells and the outflow section is circumferentially composed of six mesh cells.

According to one embodiment, the ones of the plurality of mesh cells in the inflow section have a strut width greater than strut widths of ones of the plurality of mesh cells in the transition section and outflow section.

According to one embodiment, the concave contour has a profile curvature radius of 4-6 mm and a concave depth of 1-2 mm and is located in the first and/or second stent ring on a side nearer to a proximal end of the stent.

According to one embodiment, the stent is fabricated from a nitinol alloy.

The present invention also provides a heart valve prosthesis for use in heart valve replacement, including: a heart valve; and a stent as defined above.

According to one embodiment, the heart valve is a tri-leaflet valve sewn from a three unidirectional opening valves formed of porcine pericardium that has been treated with an anti-calcification treatment.

According to one embodiment, the heart valve is sewn onto the stent by medical sutures made of polyethylene terephthalate.

The valve stent according to the present invention has a deployment portion with a concave contour which enables self-deployment of the stent and thus results in improved stent deployment accuracy and reduced operational complexity. According to the present invention, as long as the stent has not yet been completely deployed, the retrieve or relocation of the stent is allowed for correcting an improper deployment location or improper stent size. In addition, the stent has a wedge-shaped inflow section which can effectively prevent the coronary artery ostia from being obstructed and hence enables strict control of the length of a portion of the stent extending within the ventricle. This can prevent bundle branch block and other serious complications that may be caused by excessive extension of the stent in the ventricle.

BRIEF DESCRIPTION OF THE DRAWINGS

These and additional features and advantages of the present invention will be more fully understood in view of the following detailed description of merely illustrative and non-limiting embodiments thereof, in conjunction with the drawings in which.

DETAILED DESCRIPTION OF PREFERRED EMBODIMENTS

The present invention is described in greater detail below with reference to specific embodiments. In general terms, the invention relates to a heart valve prosthesis having a self-expanding stent for supporting a heart valve. Along a longitudinal axis of the self-expanding stent, it has a proximal portion, an intermediate portion and a distal portion. In the context of the present application, the proximal portion corresponds to an inflow portion of the prosthesis, and accordingly, the distal portion corresponds to an outflow portion thereof.

Figure 1:
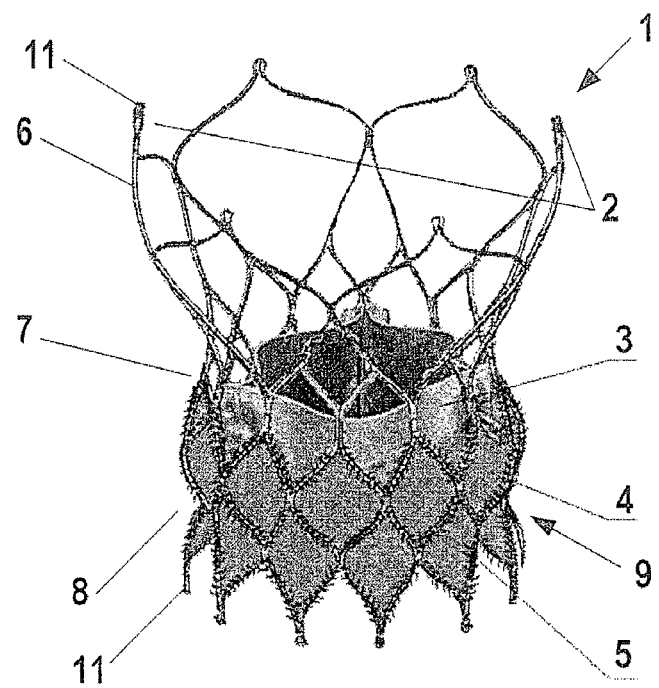
FIG. 1 is a perspective view of an exemplary heart valve prosthesis constructed in accordance with the present invention.

FIG. 1 shows an exemplary embodiment of the heart valve prosthesis according to the present invention. Specifically, the heart valve prosthesis may be an interventional aortic valve prosthesis for replacing a defective aortic valve. The valve prosthesis includes a stent 1 and a prosthetic aortic valve 3. The valve 3 is affixed to an internal surface of the stent 1, for example, by sewing. The stent 1 has a contracted configuration for delivery and an expanded deployed configuration, for example as shown in FIG. 1, which is in consistence with the native heart structure.

In the expanded deployed configuration shown in FIG. 1, the stent 1 generally appears as a mesh structure formed of multiple mesh cells and has a longitudinal axis. Specifically, the stent 1 appears as a flared mesh structure defining an outflow section 6, a transition section 7 and an inflow section 8, from the top downward along the longitudinal axis. The inflow section 8 corresponds to a portion of the prosthesis from which blood flows in when the valve works and it extends into the left ventricle after the implantation. The outflow section 6 corresponds to a portion of the prosthesis from which blood flows out when the valve works and it attaches to the ascending aorta after the implantation.

As can be perceived from FIG. 1, the stent 1 according to the present invention conically tapers from the inflow section 8 toward the transition section 7 and flares from the transition section 7 toward the outflow section 6. According to one embodiment, the inflow section 8 may have a deployed diameter of 21 mm to 30 mm, for example, 30 mm, and the outflow section 6 may have a diameter in the range of 38 mm to 43 mm, for example 43 mm, in order to enable different sizes of the stent to match various native anatomical structures with different sizes. In particular, the outflow section 6 is circumferentially composed of six mesh cells each having an area of about 0.8-1.60 cm$^2$. The six mesh cells may have the same size or different sizes within the above range. For example, adjacent two of the six mesh cells may have respectively areas of about 0.8 cm$^2$ and about 1.3 cm$^2$. In these mesh cells, the adjacent struts of the outflow section intersect at an angle of 60°-120°, more preferably, 55°-65°. Generally, two engagement structures 2 are arranged at the distal end of the outflow section 6, which are configured to guide the stent into or out of a sheath of a delivery device. After the deployment of the prosthesis, the outflow section 6 extends into the ascending aorta and is attached to the inner surface thereof and can adjust the orientation of the valve stent to make it parallel to blood flow.

With continued reference to FIG. 1, the transition section 7 of the valve stent connects the outflow section 6 with larger diameter and the inflow section 8 with smaller diameter. From the outflow section 6 toward the inflow section 8, the circumferential number of mesh cells increases gradually from 6 to 12. In the transition section, the adjacent struts intersect at an angle of 45°-55°, and each of the mesh cells has an area of about 0.7 cm$^2$.

Mesh cells are circumferentially densest in the inflow section 8 of the stent 1. In the illustrated embodiment, the inflow section 8 may comprise two or more stent rings. Each stent ring is circumferentially composed of twelve mesh cells each with an area of about 0.5-0.8 cm$^2$ and with the adjacent struts of the inflow section intersecting at an angle of 30°-65°. After the implantation of the valve prosthesis, the inflow section 8 is deployed at the native valve annulus of the aorta root. In particular, in accordance with the present invention, the inflow section 8 has a concave contour (the portion indicated by the arrow 9 in the figure) that is automatically adaptable to the structure of the native valve annulus and can thus closely adhere to the native valve annulus to achieve accurate deployment. Compared to the conventional valve prosthesis without such concave contour, in the expanded deployed configuration, the concave contour in the inflow section 8 allows self-deployment of the valve stent to result in reduced difficulty of the positioning of the valve and improved accuracy of the location. In addition, the complementary shapes can provide strong radial support which ensures closer adherence of the valve stent to the native valve annulus while creating space for valve function and effectively preventing perivalvular leakage and valve stent displacement.

Figure 5:
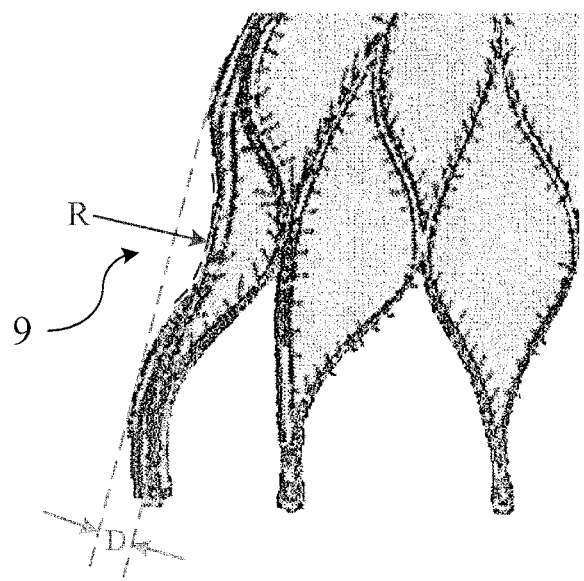
FIG. 5 is a partially enlarged view of the heart valve prosthesis.

According to a preferred embodiment, a portion of the stent corresponding to the concave contour may employ relatively larger mesh cells with respect to other mesh cells of the inflow section 8. For example, each mesh cell at the concave contour 9 may have an area of about 0.6-0.8 cm$^2$, and other mesh cells in the inflow section 8 may have an area of about 0.5-0.6 cm$^2$. The adoption of a larger mesh cell area at the concave contour 9 can improve the adherence of the concave contour 9 to the native valve annulus, especially when there are large calcified masses at the native valve annulus. In a conventional stent circumferentially composed of 15 mesh cells in the inflow section, the large calcified masses at the native valve annulus cannot pass through the mesh cells of the inflow section, which may cause insufficient adherence of the stent to the native valve annulus. While in the stent 1 of the present invention, the inflow section 8 circumferentially composed of 12 mesh cells and the concave contour 9 having even larger cell size than other cells in the inflow section 8 can ensure large calcified masses to pass through the mesh cells, so that a more sufficient adherence of the stent to the native valve annulus can be achieved, which may effectively prevent perivalvular leakage after deployment of the stent 1. The concave contour may have a profile curvature radius R of 4-6 mm and a concave depth D of 1-2 mm (see FIG. 5). Such a design has taken into consideration both of fatigue resistance and positioning stability of the stent. If a too small curvature radius or a too small concave depth is chosen, the duration or life cycle of the stent 1 may be deteriorated, and the stent 1 may likely to get damaged after bending. On the other hand, if a too large curvature radius or a too large concave depth is chosen, the stent may not be able to perfectly match with and closely adhere to the native valve annulus, and hence the positioning stability will be influenced. According to a preferred embodiment, the concave contour 9 may be formed at a location in the first or second stent ring or spans the first and second stent rings from a side of the inflow section 8 nearer to the proximal end of the stent 1. It can be understood that, the complementary shapes of the native valve annulus and concave contour impart a self-deployment function to the valve prosthesis according to the present invention. Additionally, the concave contour is of great significance to the relocation and retrieve of the stent. More precisely, the concave contour can be complementary in shape to the native valve annulus when stent deployed. For example, when the inflow section even together with the transition section, is deployed from the delivery sheath, the deployed inflow section, especially the portion corresponding to the concave contour, can be soon inflated to a configuration close to its fully expanded deployed configuration and thus allow the concave contour to spontaneously adhere to the aortic annulus. At this moment, a physician may monitor the deployment, for example, by one or several of the various existing imaging technologies. If the stent is found unable to perfectly adhere to the native valve annulus due to an improper deployment location or an improper size of the valve, the tension of the deployed part of the stent, i.e. the concave contour and only one to two stent rings proximal to the concave contour, will not impede the part from being retrieved to the delivery sheath, thus making it possible to relocate the stent or deliver the valve again after the valve is replaced.

The expanded deployed configuration may be accomplished by a metal alloy treated with technologies known in this art. For example, the stent 1 is desirably a self-expanding stent which can be fabricated by laser-sculpting a metal alloy tube and then molding the tube by a series of thermal treatments (e.g., shaping, grinding and polishing) to a structure with desired shape, superelasticity and shape memory ability. The metal alloy tube may be fabricated from a shape memory material such as a nitinol alloy.

Figure 2:
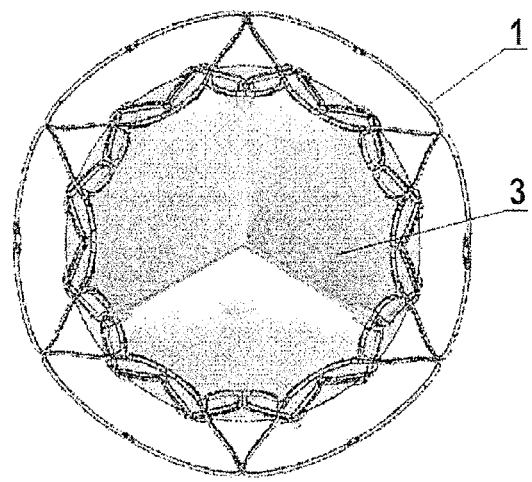
FIG. 2 is an end view of the heart valve prosthesis of FIG. 1.

The aortic valve 3 is affixed within the inflow section 8 of the stent. As shown in the side view of FIG. 2, the valve 3 is a tri-leaflet valve sewn from three unidirectional opening valves formed of porcine pericardium that has been treated with an anti-calcification treatment. The affixation with the inflow section 8 may be accomplished by sewing the valve 3 with medical sutures 5 onto a skirt 4 that has been sewn onto the inflow section 8 of the stent. The anti-calcification treatment before the sewing allows the valve 3 to be calcified in the in-vivo environment at a significantly reduced speed and to thus have a significantly extended fatigue life. The skirt 4 may be made of polyethylene terephthalate (PET) or porcine pericardium that has been treated with an anti-calcification treatment.

As noted above, the stent 1 is preferably fabricated from a nitinol alloy, which is a shape memory metal material with superelasticity, and the medical sutures 5 are made of PET preferably.

As shown in FIG. 1, ends of the inflow section 8 and outflow section 6 of the stent 1 according to the present invention are slightly contracted so as to be "tapered ends" 11. An angle of the contraction may range from 8° to 12°, with 10° being more preferred, in order to prevent damage of the surrounding tissue that can be caused by the stent during its adherence to the left ventricle and aortic inner wall (as more apparent from FIG. 4).

Figure 4:
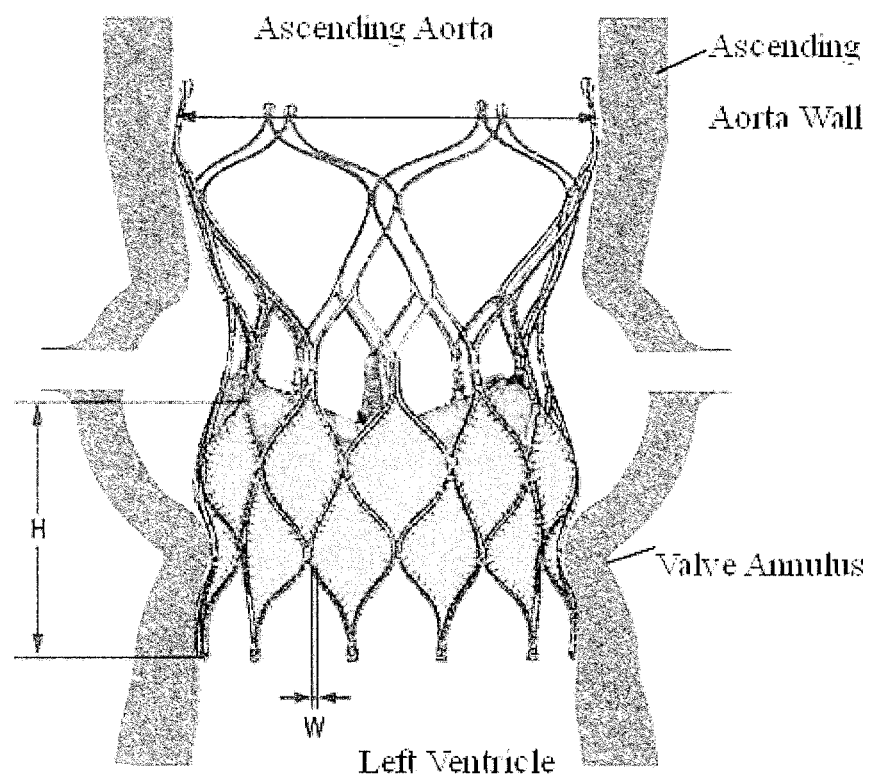
FIG. 4 is a side view of a heart valve prosthesis according to the present invention which is deployed in the body of a patient.

The heart valve prosthesis according to the present invention offers a wide range of advantages. FIG. 4 schematically depicts a valve prosthesis according to the present invention in a deployed state. As can be found in FIG. 4, the concave contour that is complementary to the structure of the native valve annulus at the deployed position of the inflow section allows the valve stent to closely adhere to the native valve annulus to achieve high deployment accuracy as well as prevention of displacement and perivalvular leakage. In addition, the portion of the inflow section corresponding to the concave contour that employs relatively larger mesh cells can effectively avoid perivalvular leakage. The perivalvular leakage may be caused by insufficient adherence between the stent and the native valve annulus in the case that there are large calcified masses at the patient's native valve annulus with which too dense mesh cells are less capable of deformation in accordance. Obviously, this design with an inflow section 8 composed of 12 mesh cells in each stent ring and with a concave contour constructed by larger cells than other cells of the inflow section 8 is advantageous over the conventional stents circumferentially composed of 15 mesh cells in the inflow section.

As described above, the conical inflow section of the stent is diametrically larger at the proximal end and has a lager strut width W. This imparts higher strength to this section, enabling the stent to be securely deployed with an enhanced ability to resist displacement after implantation.

In addition, the capability of the stent of anatomically accurate deployment allows strict control of the length of a portion of the valve stent extending in the left ventricle. For example, only one or two rings of struts may be arranged proximal to the concave contour along the longitudinal axis, so that the likelihood of damage to the left ventricle caused by a long extending portion of the stent can be greatly reduced.

In addition to the conical profile of the inflow section, the stent according to the present invention also employs a proper full height H of the skirt to ensure that the deployed stent do not obstruct blood flow to the coronary arteries.

Further, the open design (i.e., larger mesh cells) of the transition section of the valve stent and outflow section makes the stent possible to conform to the native structure to ensure the valve to work normally, even the native valve annulus and ascending aorta are in a non-coaxial configuration. And the outflow section extending in the ascending aorta have good adherence to the ascending aorta.

Figure 3:
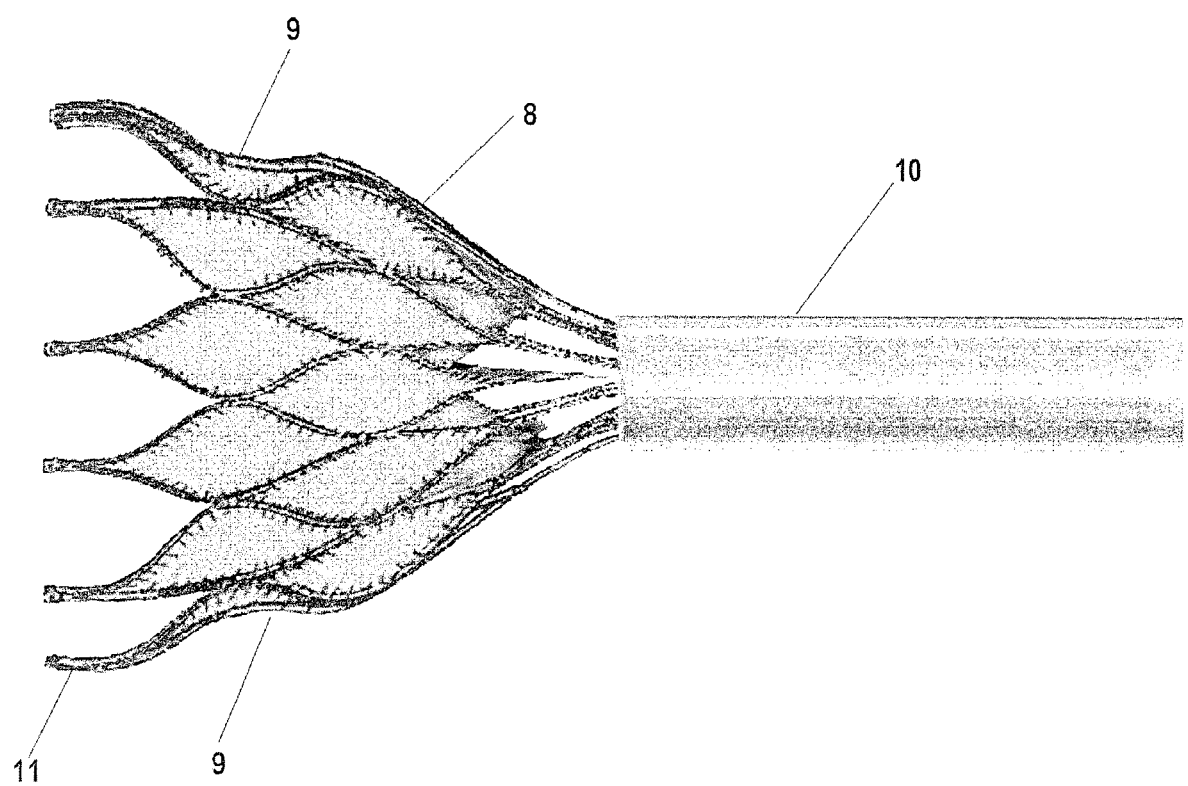
FIG. 3 is a perspective view of a heart valve prosthesis according to the present invention in a delivery configuration when the heart valve prosthesis is partially deployed.

A method for implanting the heart valve prosthesis according to the present invention into the body of the patient are described below, wherein the implantation of an aortic valve is described as an example. The method generally includes the steps of:

1. measuring a size of the patient's aortic annulus by transesophageal echocardiography or CT and selecting the said interventional prosthetic aortic valve of a size consistent with the measurement results;

2. loading the prosthetic aortic valve stent into a sheath 10 of a delivery device (not shown) in ice water;

3. puncturing the femoral artery of the patient who is in general (or local) anesthesia, delivering the sheath 10 in the puncture, and directing a guide wire (not shown) through the abdominal aorta, through the thoracic aorta, through the aortic valve and finally into the left ventricle, establishing the delivery path;

4. delivering passing the sheath 10 loaded with the prosthetic aortic valve stent to the aortic annulus along the guide wire and partially deploying the valve stent, wherein FIG. 3 shows the stent which is partially deployed;

5. monitoring the deployment of the valve stent by imaging to allow adjustment of the deployment location when the deployment is found improper, deploying and inflating the valve stent to replace the native aortic valve when it has been correctly positioned, and verifying whether aortic valve regurgitation occurs by aortic-root angiography;

6. retrieving the sheath 10 along the guide wire and then retrieving the wire;

7. evaluating the location and effectiveness of the deployment on the basis of transesophageal echocardiograms and another imaging procedure, followed by closing the vascular puncture by sutures.

While the invention has been described above with reference to specific embodiments, it should be understood that these embodiments are merely for the purpose of illustration and description and do not limit the scope of the invention in any way. It should be also understood that various changes and modifications that may be made by those skilled in the art in view of the above teachings are all also within the scope of the invention as defined in the appended claims.

What is claimed is:

1. A stent for use in a heart valve prosthesis, the stent configured to support a heart valve and comprising, along a longitudinal axis and from a proximal end to a distal end, an inflow section, a transition section and an outflow section, the stent having a contracted delivery configuration and an expanded deployed configuration, wherein in the expanded deployed configuration, the inflow section defines a concave contour that is complementary to a structure of a native valve annulus such that the concave contour closely adheres to a native valve annulus upon proper deployment of the stent; wherein the concave contour is located in a first or a second stent ring of the stent from the proximal end of the stent or the concave contour spans the first and second stent rings; and wherein the stent comprises a mesh having a plurality of mesh cells and ones of the plurality of mesh cells in the inflow section corresponding to the concave contour are larger than remaining ones of the plurality of mesh cells in the inflow section, each of the ones of the plurality of mesh cells in the inflow section corresponding to the concave contour having an area of about 0.6-0.8 cm$^2$, and each of the remaining ones of the plurality of mesh cells in the inflow section having an area of about 0.5-0.6 cm$^2$.

2. The stent according to claim 1, wherein each of the mesh cells of the outflow section has an area of about 0.8-1.60 cm$^2$.

3. The stent according to claim 1, wherein the concave contour has a profile curvature radius of 4-6 mm and a concave depth of 1-2 mm.

4. The stent according to claim 1, wherein the stent is a self-expanding stent.

5. The stent according to claim 1, wherein in the expanded deployed configuration, the stent conically tapers from the inflow section toward the transition section and flares from the transition section toward the outflow section.

6. The stent according to claim 1, wherein the inflow section has a proximal end slightly contracted.

7. The stent according to claim 6, wherein an angle of the contraction ranges from 8° to 12°.

8. The stent according to claim 1, wherein the outflow section has a distal end slightly contracted.

9. The stent according to claim 8, wherein an angle of the contraction ranges from 8° to 12°.

10. The stent according to claim 1, wherein the inflow section is circumferentially composed of twelve mesh cells.

11. The stent according to claim 10, wherein adjacent struts of the inflow section intersect at an angle of 30°-65°.

12. The stent according to claim 10, wherein the outflow section is circumferentially composed of six mesh cells.

13. The stent according to claim 12, wherein adjacent struts of the outflow section intersect at an angle of 60°-120°.

14. The stent according to claim 12, wherein adjacent struts of the outflow section intersect at an angle of 55°-65°.

15. The stent according to claim 12, wherein a circumferential number of mesh cells transitions from 6 to 12 at the transition section.

16. The stent according to claim 1, wherein the ones of the plurality of mesh cells in the inflow section have a strut width greater than strut widths of ones of the plurality of mesh cells in the transition section and in the outflow section.

17. The stent according to claim 1, wherein the stent is fabricated from a nitinol alloy.

18. A heart valve prosthesis for use in heart valve replacement, comprising:
   a heart valve; and
   a stent configured to support the heart valve and comprising, along a longitudinal axis, an inflow section, an outflow section and a transition section between the inflow section and the outflow section, the stent having a contracted delivery configuration and an expanded deployed configuration,
   wherein in the expanded deployed configuration, the inflow section defines a concave contour that is complementary to a structure of a native valve annulus such that the concave contour closely adheres to the native valve annulus upon proper deployment of the stent; wherein the concave contour is located in a first or a second stent ring of the stent from the proximal end of the stent or the concave contour spans the first and second stent rings; and wherein the stent comprises a mesh having a plurality of mesh cells and ones of the plurality of mesh cells in the inflow section corresponding to the concave contour are larger than remaining ones of the plurality of mesh cells in the inflow section, each of the ones of the plurality of mesh cells in the inflow section corresponding to the concave contour having an area of about 0.6-0.8 cm$^2$, and each of the remaining ones of the plurality of mesh cells in the inflow section having an area of about 0.5-0.6 cm$^2$.

19. The heart valve prosthesis according to claim 18, wherein the heart valve is a tri-leaflet valve sewn from a one-way tri-leaflet pericardial valve formed of porcine pericardium that has been treated with an anti-calcification treatment.

20. The heart valve prosthesis according to claim 18, wherein the heart valve is sewn onto the stent by medical sutures made of polyethylene terephthalate.

\* \* \* \* \*